United States Patent [19]
High

[11] Patent Number: 5,843,113
[45] Date of Patent: Dec. 1, 1998

[54] ENDOCYSTOTOMY TOOL

[76] Inventor: Kenneth High, P.O. Box 1415, Dillon, Mont. 59725

[21] Appl. No.: 729,796

[22] Filed: Oct. 8, 1996

[51] Int. Cl.⁶ .................................................. A61M 17/00
[52] U.S. Cl. ........................................... 606/184; 604/164
[58] Field of Search ............................... 606/1, 170, 184, 606/185; 604/164; 128/749–754, 898; 623/8

[56] References Cited

U.S. PATENT DOCUMENTS

| | | |
|---|---|---|
| 4,723,547 | 2/1988 | Kullas et al. ............................ 606/185 |
| 5,047,039 | 9/1991 | Avant et al. . |
| 5,152,749 | 10/1992 | Giesy et al. . |
| 5,232,443 | 8/1993 | Leach . |
| 5,242,427 | 9/1993 | Bilweis .................................. 606/185 |
| 5,348,541 | 9/1994 | Lyell . |

*Primary Examiner*—Michael Powell Buiz
*Assistant Examiner*—William W. Lewis

[57] ABSTRACT

A new endocystotomy tool for suprapubic cystostomy has a rigid sound, said rigid sound having standard configuration such as a standard Van Buren urethral sound. Said rigid sound having a distal end, said distal end having a removable tip, said removable tip being rounded. A second embodiment of said new endocystotomy tool for suprapubic cystostomy has an extendable trocar slidably seated within the rigid sound. Said second embodiment of said new endocystotomy tool for suprapubic cystostomy having a proximate end thereof which is provided with an insufflation port and a spring loaded plunger, which spring loaded plunger activates said extendable trocar. Either a catheter, a sheath, or a cystoscope is passed inside the tip of the new endocystotomy tool and secured therein. Thus the catheter, sheath, or cystoscope easily slides through the abdominal wall and bladder, i.e., the diameter of the catheter, sheath, or the cystoscope being smaller than the diameter of the new endocystotomy tool.

6 Claims, 2 Drawing Sheets

ENDOCYSTOTOMY TOOL

BACKGROUND OF THE INVENTION

1. Field of the Invention

This invention pertains generally to improvements relating to catheters, suprapubic bladder catheter insertion, and, more particularly, to a new endocystotomy tool having a removable tip.

2. Description of the Prior Art

Temporary or permanent bypass of the urethra via suprapubic catheter drainage of the bladder is an important adjunct in many pelvic operations. Suprapubic cystostomy has traditionally been performed either by trocar percutaneous insertion or by an open operative procedure. "Inside-out" catheter placement is generally accepted as a safer and quicker method of urinary catheter placement. Accurate and safe placement of a catheter, such as a Foley catheter, is essential to minimize stress and trauma on the patient.

Potential problems with percutaneous suprapubic "outside-in" catheter placement include difficulty in hitting the bladder, leading to extra-vesical deployment, difficulty in controlling depth of penetration, bladder invagination prior to bladder wall puncture, the possibility of poor catheter/bladder wall seal, and injury to intra-abdominal viscera. These catheters require suture fixation to the skin, but despite this often become dislodged, especially when used in children, and are also limited by their small lumenal diameter.

The chance of injury to the intra-abdominal viscera is decreased by approximation of the bladder wall to the anterior abdominal wall during the "inside-out" insertion process.

Prior art discloses a Lowsley retractor which is passed through the urethra into the bladder and used to approximate the bladder wall to the anterior abdominal wall. A suprapubic incision is made and the Lowsley retractor exited from the bladder through the abdominal wall via the incision. The Lowsley retractor has jaws that open to grasp the catheter and pull the same back into the bladder. Disadvantages of the Lowsley retractor are that the tip is always larger when the jaws are spread and the catheter grasped, making it more difficult to bring through the abdominal wall and bladder wall. It is possible to turn the bladder wall inside out, and possible for the catheter to become dislodged and fall off before entering the bladder, thus extending operating time, potentially not properly placing the catheter inside the bladder, and potentially adding to bladder trauma at surgery.

Prior art teaches suprapubic catheter placement by making an abdominal incision of approximately 3" to 4" and cutting down to the bladder, opening the bladder, inserting the catheter then suturing the bladder, abdominal fascia, subcutaneous tissue and skin. A surgical drain is often necessary with this procedure. Disadvantages of this procedure include the need for anesthesia, the use of an operating and a recovery room, much more postoperative pain and discomfort, a significantly longer hospital stay and much higher costs.

SUMMARY OF THE INVENTION

The purpose of the present invention is to provide a new endocystotomy tool and particularly a urinary catheter/sound tool which can solve the aforementioned problems permitting placement of a urinary catheter or a cystoscope into the bladder in a safer and less stressful manner. Urethral sounds are familiar to all urologists.

The new endocystotomy tool is passed into the bladder using the same technique as other sounds. The new endocystotomy tool is then presented beneath the abdominal wall and either a small cut-down incision made against the slotted, removable tip, or in another embodiment, a trocar of the new endocystotomy tool presented to make an inside-out opening into the bladder. The removable tip end of the new endocystotomy tool is then exited the opening into the bladder and abdominal wall and held in exited position by means of a securing pin passed through an opening in the removable tip. When the surgeon is next ready to proceed, the securing pin is removed from the removable tip and the removable tip is removed from the new endocystotomy tool. Either a catheter, a sheath, or a cystoscope is passed inside the open end of the new endocystotomy tool from where the removable tip has been removed and secured therein. Thus the catheter, sheath, or cystoscope easily slides through the abdominal wall and bladder, i.e., the diameter of the catheter, sheath, or the cystoscope is smaller than the diameter of the new endocystotomy tool. Because the junction of the catheter, sheath, or cystoscope to the new endocystotomy tool is smooth and of a uniform diameter, the complications potentially encountered with using the Lowsley sound or the "inside-out" techniques are far less likely to occur.

It is an object of the present invention to provide a new endocystotomy tool for placement of a urinary bladder catheter or insertion of a cystoscope into the bladder.

Another object of the present invention is to provide a new endocystotomy tool having a removable tip for securing a catheter, sheath, or cystoscope thereto.

Another object of the present invention is to provide a new endocystotomy tool for insufflation of the bladder prior to opening thereof.

Other objects and novel features of the present invention will become apparent from the following detailed description of the present invention when considered in conjunction with the accompanying drawings wherein like reference numbers identify like parts throughout.

IN THE DRAWINGS

DESCRIPTION OF THE PREFERRED EMBODIMENT

Figure 1:
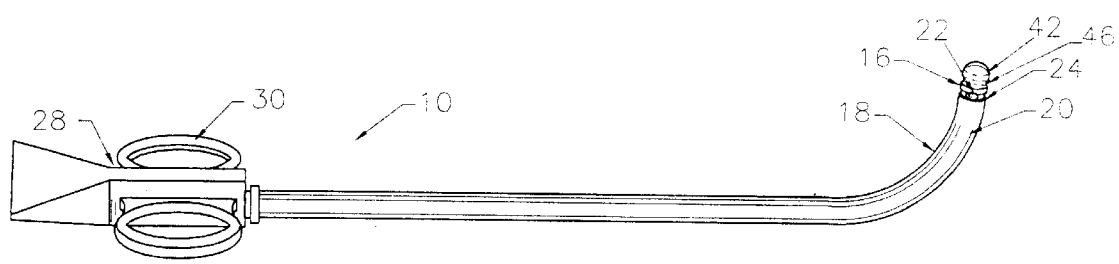
FIG. 1 is a perspective view of a first embodiment of the new endocystotomy tool of the present invention showing the rigid sound and the removable tip attached thereto.

Referring now more particularly to the drawings, reference numerals will be used to denote like parts or structural features in the different views.

A first embodiment of the new endocystotomy tool of the present invention is illustrated in FIG. 1 comprising a rigid sound 10 having a standard configuration, such as a standard Van Buren urethral sound and a removable tip 16 on a distal end 18 of the rigid sound 10. Preferably, the new endocystotomy tool of the present invention is made of surgical stainless steel, synthetic resin, molded plastic, or such other suitable material.

Figure 2:
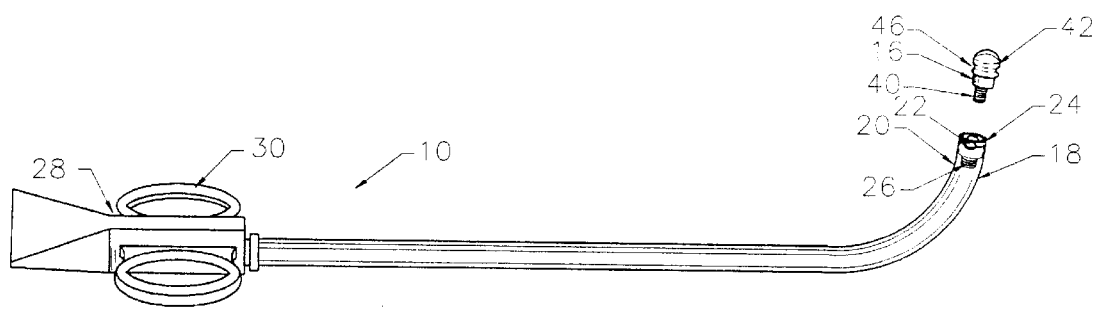
FIG. 2 is a perspective view of a first embodiment of the new endocystotomy tool of the present invention showing the rigid sound and the removable tip removed therefrom.

As seen in FIGS. 1 and 2, the distal end 18 of the rigid sound 10 is arcuately curved at a 90 degree angle to its longitudinal axis to achieve a standard configuration, such as a standard Van Buren urethral sound. The rigid sound 10 may be hollow interiorly throughout but must be hollow at the extreme distal end 20. The extreme distal end 20 of the rigid sound 10 has a hole 22 therethrough, said hole 22 being through the extreme distal end 20 of the rigid sound 10 on a plane parallel with the longitudinal axis of the rigid sound 10. The extreme distal end 20 of the rigid sound 10 has a groove 24 circumscribed around the outside diameter thereof on a plane perpendicularly intersecting the openings of said hole 22 therethrough. The extreme distal end 20 of the rigid sound 10 has female threads 26 on the hollow interior thereof, which female threads 26 complement and engage male threads 40 of said removable tip 16.

As seen in FIG. 2, a removable tip 16 attaches and secures to the extreme distal end 20 of the rigid sound 10. Said removable tip 16 has male threads 40 which complement and engage said female threads 26 on the extreme distal end 20 of the rigid sound 10 and accommodate screwing of the removable tip 16 onto the extreme distal end 20 of the rigid sound 10 and securing the same thereby. The removable tip 16 is rounded or bullet shaped on the end 42 distal to the male threads 40. The removable tip 16 has a slot 44 across the end 42 distal to said male threads 40, said slot 44 being on a plane parallel yet perpendicular to the longitudinal axis of said rigid sound 10 when said removable tip 16 is securely threaded onto said rigid sound 10. The removable tip 16 has a hole 46 therethrough, said hole 46 being on a plane perpendicular to the longitudinal axis of the rigid sound 10 when said removable tip 16 is securely threaded onto said rigid sound 10. Said hole 46 being provided to accommodate leverage to tighten or loosen said removable tip 16 on the rigid sound 10 as well as for placement of a pin or other apparatus to secure the distal end 18 of the rigid sound 10 exterior to the abdominal wall after passing the distal end 18 of the rigid sound 10 therethrough from the inside-out.

Said rigid sound 10 has a proximate end 28. Said proximate end 28 of the rigid sound 10 is provided with an attachment 30 for the physical manipulation of the rigid sound 10.

Figure 3:
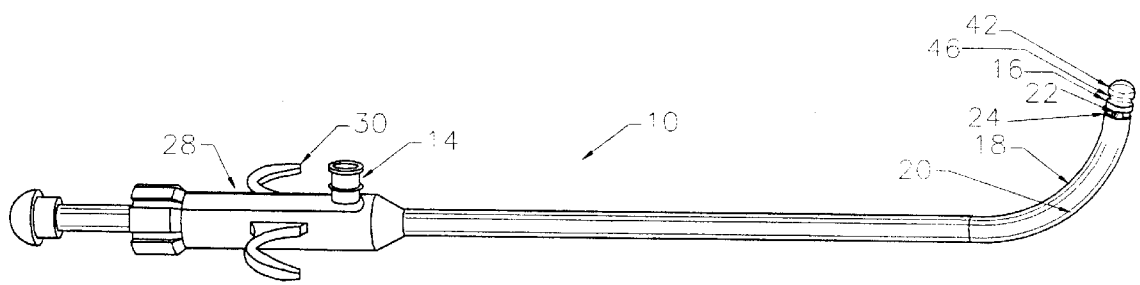
FIG. 3 is a perspective view of a second embodiment of the new endocystotomy tool of the present invention showing the rigid sound and the removable tip attached thereto and further showing the extendable trocar.
Figure 4:
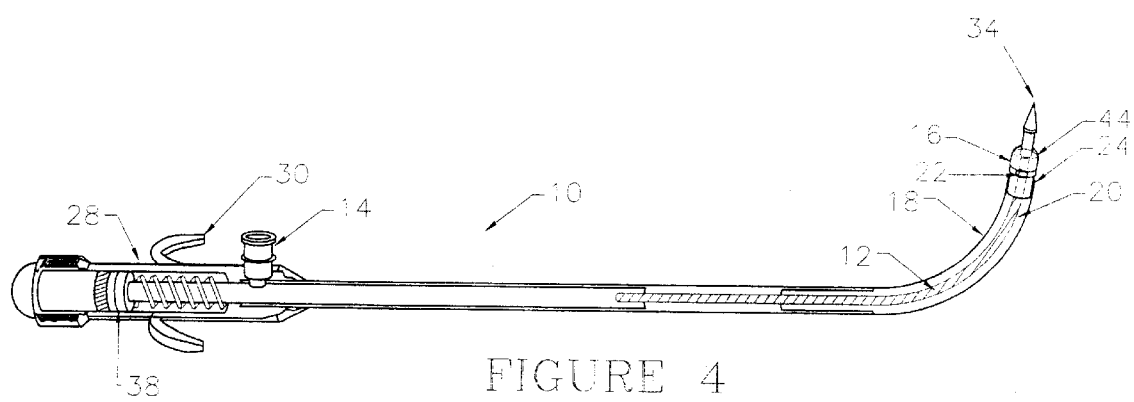
FIG. 4 is a perspective view of a second embodiment of the new endocystotomy tool of the present invention showing the rigid sound and the removable tip attached thereto and further showing the extendable trocar extended.
Figure 5:
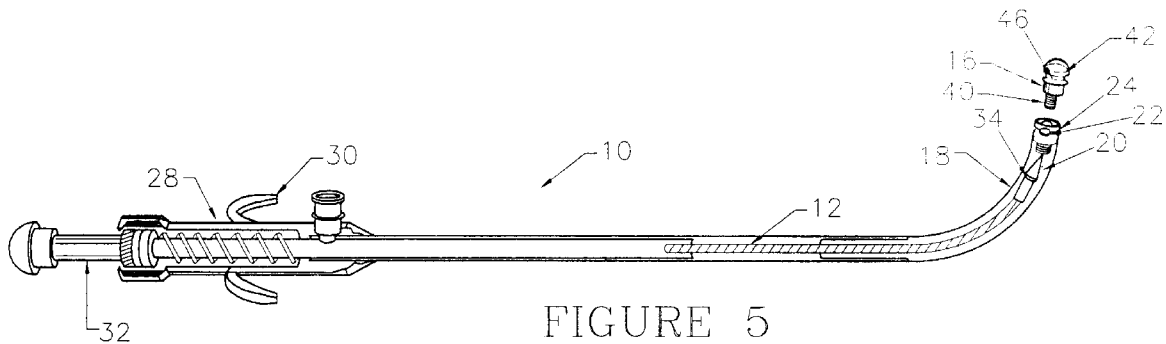
FIG. 5 is a perspective view of a second embodiment of the new endocystotomy tool of the present invention showing the rigid sound and the removable tip removed therefrom and further showing the extendable trocar.

A second embodiment of the new endocystotomy tool of the present invention is illustrated in FIGS. 3, 4, and 5 comprising four principal components: a rigid sound 10 having a standard configuration, such as a standard Van Buren urethral sound, an extendable trocar 12 slidably seated within the rigid sound 10, an insufflation port 14 mounted on the rigid sound 10, and a removable tip 16 on a distal end 18 of the rigid sound 10. The removable tip 16 is hollow therethrough to slidably accommodate said cutting point 34 on the extreme distal end of the extendable trocar 12.

Said second embodiment of said rigid sound 10 has a proximate end 28. The proximate end 28 of the rigid sound 10 is enlarged relative to the distal end 18. The proximate end 28 of the rigid sound 10 is provided with an insufflation port 14 mounted and secured thereon. The proximate end 28 of the rigid sound 10 is provided with finger attachments 30 for the physical manipulation of the rigid sound 10. The proximate end 28 of the rigid sound 10 is provided with a spring loaded plunger 32, which spring loaded plunger 32 activates an extendable trocar 12 slidably seated within the rigid sound 10. The extendable trocar 12 is sufficiently resiliently flexible so as to be able to slidably seat yet slide longitudinally within the hollow interior of the rigid sound 10. The extendable trocar 12 is provided with a cutting point 34 on the extreme distal end thereof. The cutting point 34 on the extreme distal end of the extendable trocar 12 may be removable and disposable. Such a removable cutting point may be of surgical steel, a material such as "Ultem", or other suitable material. The spring loaded plunger 32 is provided with an "o" ring seal 38, which "o" ring seal 38 prevents fluid from leaking therefrom during insufflation. The "o" ring seal 38 is made of Vitron or other suitable material.

Said second embodiment has a removable tip 16, which removable tip 16 attaches and secures to the extreme distal end 20 of the rigid sound 10. Said removable tip 16 has male threads 40 which complement and engage said female threads 26 on the extreme distal end 20 of the rigid sound 10 and accommodate screwing of the removable tip 16 onto the extreme distal end 20 of the rigid sound 10 and securing the same thereby. The removable tip 16 is rounded or bullet shaped on the end 42 distal to the male threads 40. The removable tip 16 is hollow therethrough to slidably accommodate said cutting point 34 on the extreme distal end of the extendable trocar 12. The removable tip 16 has a hole 46 therethrough, said hole 46 being on a plane perpendicular to the longitudinal axis of the rigid sound 10 when said removable tip 16 is securely threaded onto said rigid sound 10. Said hole 46 being provided to accommodate leverage to tighten or loosen said removable tip 16 on the rigid sound 10 as well as for placement of a pin or other apparatus to secure the distal end 18 of the rigid sound 10 exterior to the abdominal wall after passing the distal end 18 of the rigid sound 10 therethrough from the inside-out.

In the use of either embodiment of the new endocystotomy tool of the present invention, the distal end 18 of the rigid sound 10 with the removable tip 16 securely attached is advanced through the urethra into the bladder. With said second embodiment of the new endocystotomy tool of the present invention, the bladder may then be insufflated and thus distended by the introduction of suitable fluid. With said second embodiment of the new endocystotomy tool of the present invention the bladder is insufflated through the insufflation port 14, said insufflation port 14 being of a luer nature such as a Luer-Loc fitting. With either embodiment of the new endocystotomy tool of the present invention, the removable tip 16 is presented in the suprapubic area, impinging on the front wall of the bladder and "tenting" the bladder so that the removable tip 16 can be felt under the skin below the umbilicus. Presenting the removable tip 16 in the suprapubic area is minimally invasive in that such presentation of a rounded tip tends to slide by rather than lacerate or sever blood vessels.

The surgeon may then locate the slot 44 on the removable tip 16 and make a small cut-down incision over said slot 44. If the surgeon is utilizing the second embodiment of the endocystotomy tool of the present invention and does not desire to make a small cut-down incision from the outside-in, the surgeon may apply pressure to the spring loaded plunger 32 which in turn activates the extendable trocar 12 forcing the cutting point 34 on the extreme distal end of the extendable trocar 12 through the bladder and abdominal wall in inside-out manner.

Figure 6:
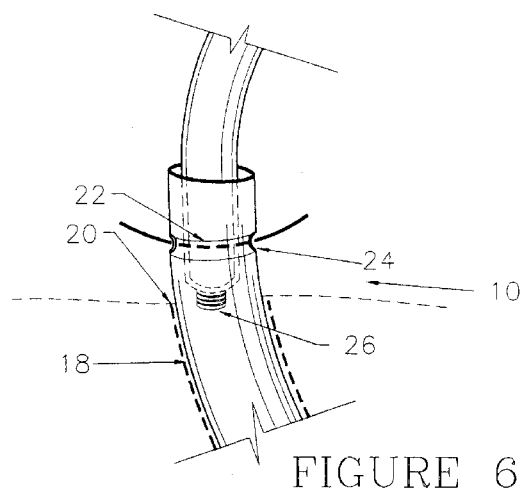
FIG. 6 shows the new endocystotomy tool of the present invention extended through the bladder and abdominal wall and having a catheter attached thereto.
Figure 7:
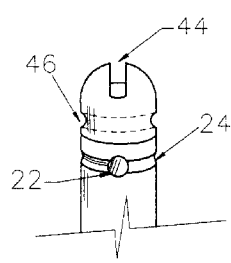
FIG. 7 shows the tip of the new endocystotomy tool in detail.

As seen in FIG. 6, the distal end 18 of the rigid sound 10 with the removable tip 16 secured thereon is then advanced through the abdominal wall and skin. The removable tip 16 is then unscrewed from the distal end 18 of the rigid sound 10 and a pin or other holding device passed through the hole 22 through the extreme distal end 20 of the rigid sound 10 securing the rigid sound 10 exterior on the abdominal wall while the surgeon accomplishes other tasks. The surgeon may then either insert the end of a catheter, a sheath, or a cystoscope into the distal end 18 of the rigid sound 10 beyond the hole 22 therethrough, said distal end 18 of the rigid sound 10 being hollow to accommodate attachment of a catheter, a sheath, or cystoscope. If a catheter is being used, the catheter is then secured into the distal end 18 of the rigid sound 10 by a suture tie being placed through said hole 22, the catheter, and said groove 24, and said suture further being secured to said rigid sound 10 by being tied in said groove 24 thereby securing the catheter within said rigid sound 10.

The catheter, sheath, or cystoscope is then drawn into the bladder and urethra by withdrawal of the rigid sound 10. The rigid sound 10 is withdrawn through the urethral meatus with the attached catheter and the suture is cut, severing the connection between the catheter and the rigid sound 10. The catheter is withdrawn back into the bladder, the balloon inflated, the catheter irrigated and the catheter is secured.

While particular embodiments of the invention have been shown and described, it will be understood that the invention is not limited thereto, since modifications may be made that will become apparent to those skilled in the art.

What is claimed is:

1. A new endocystotomy tool comprising:

a rigid sound, said rigid sound having a distal end;

said distal end being hollow and having a hole therethrough;

said distal end having a groove circumscribed around an outside diameter thereof;

said distal end being arcuately curved at a 90 degree angle to a longitudinal axis of said rigid sound;

said hole through said distal end of said rigid sound being on a plane parallel with said longitudinal axis of said rigid sound;

said groove circumscribed around said outside diameter of said distal end of said rigid sound intersecting perpendicularly said hole through said distal end of said rigid sound;

said distal end of said rigid sound having female threads on said hollow interior thereof;

said rigid sound having a proximate end;

said proximate end of said rigid sound having an attachment for manipulation mounted thereon;

said rigid sound having a removable tip on said distal end, said removable tip having a rounded face;

said removable tip having male threads, said male threads complementing and engaging said female threads in said distal end of said rigid sound;

said removable tip having a slot, said slot being across said rounded face of said removable tip;

said removable tip having a hole through said rounded face;

said rigid sound being hollow interiorly throughout;

said proximate end being enlarged relative to said distal end of said rigid sound;

said proximate end having an insufflation port mounted thereon;

said proximate end of said rigid sound having a plurality of two finger attachments mounted thereon;

said proximate end of said rigid sound having a spring loaded plunger;

said rigid sound having an extendable trocar, said extendable trocar being resiliently flexible and slidably seating longitudinally within the hollow interior of said rigid sound;

said extendable trocar being provided with a cutting point on a distal end thereof;

said extendable trocar being activated by said spring loaded plunger;

said spring loaded plunger being provided with a seal, said seal preventing fluid from leaking therefrom during insufflation; and, said removable tip being hollow therethrough to accommodate said cutting point of said extendable trocar.

2. The new endocystotomy tool according to claim 1 wherein said seal on said spring loaded plunger further comprises an "o" ring.

3. The new endocystotomy tool according to claim 1 wherein said insufflation port further comprises a luer connector.

4. The new endocystotomy tool according to claim 1 further comprising surgical stainless steel.

5. The new endocystotomy tool according to claim 1 further comprising synthetic resin.

6. The new endocystotomy tool according to claim 1 further comprising molded plastic.

* * * * *